(12) United States Patent
Ling et al.

(10) Patent No.: US 7,195,595 B2
(45) Date of Patent: Mar. 27, 2007

(54) METHOD AND APPARATUS FOR MONITORING THE EFFICACY OF FLUID RESUSCITATION

(75) Inventors: Geoffrey Ling, Ellicott City, MD (US); Michael J. E. Campbell, Meredith, NH (US)

(73) Assignee: Nova Technology Corporation, Portsmouth, NH (US)

( * ) Notice: Subject to any disclaimer, the term of this patent is extended or adjusted under 35 U.S.C. 154(b) by 0 days.

(21) Appl. No.: 10/908,681

(22) Filed: May 23, 2005

(65) Prior Publication Data

US 2006/0116587 A1 Jun. 1, 2006

Related U.S. Application Data

(60) Provisional application No. 60/573,296, filed on May 21, 2004.

(51) Int. Cl.
*A61B 5/02* (2006.01)
*A61B 5/05* (2006.01)

(52) U.S. Cl. .................................. 600/485; 600/547

(58) Field of Classification Search ............... None
See application file for complete search history.

(56) References Cited

U.S. PATENT DOCUMENTS 6,370,426 B1   4/2002  Campbell et al. ........... 600/547
6,628,975 B1*  9/2003  Fein et al. .................. 600/323

* cited by examiner

*Primary Examiner*—Robert L. Nasser
(74) *Attorney, Agent, or Firm*—George A. Herbster

(57) ABSTRACT

Relative Mean Arterial Pressure values are obtained non-invasively using a probe to obtain moisture measurements at a selected site on a subject. A control collects data samples. A converter produces a relative value of Mean Arterial Pressure (MAP) in response to the collected data (DPM) in accordance with a correlation defined by:

$MAP = (DPM - DPM(0))/K(I)$.

16 Claims, 4 Drawing Sheets

METHOD AND APPARATUS FOR MONITORING THE EFFICACY OF FLUID RESUSCITATION

FIELD OF THE INVENTION

This invention generally relates to the diagnosis of trauma-induced shock and more specifically to a method and apparatus for providing such diagnoses by non-invasive procedures.

DESCRIPTION OF RELATED ART

In various instances of trauma, victims often suffer resultant hemorrhagic shock. Hemorrhagic shock, if not promptly treated, can be a significant cause of trauma-related deaths. In fact, hemorrhagic shock is a leading cause of combat casualties.

Standard therapy for hemorrhagic shock is by means of fluid resuscitation to make up blood loss. Monitoring fluid resuscitation involves determining end organ perfusion and the effects of different levels of shock on the underlying cellular physiology. This determination is key to determining the timing and rate of fluid administration and the levels of resuscitation. Typically, Mean Arterial Pressure (MAP) is the variable or parameter used to monitor fluid resuscitation therapy, but accepted methods for measuring MAP are highly invasive.

At a hospital the medical staff and facilities are available for measuring MAP in a safe environment. That is, at a hospital there are sophisticated personnel for performing invasive procedures and interpreting the results. Sterile conditions exist for such invasive procedures.

However, these hospital conditions do not exist at a trauma site, such as a battlefield or accident site. Even if personnel were available for performing the procedures for measuring MAP, the unavailability of required equipment, conditions and trained personnel to interpret the results prohibit the use of such methods for battlefield use. Moreover, the environment at a trauma site is not conducive to optimal patient safety during the performance of any invasive procedure.

Fluid resuscitation therapy should begin as soon as possible and the levels of fluid administration should be controlled to an optimum rate for the trauma patient. Any delay required to transport a trauma victim to a hospital may detract from the effectiveness of any attempts at fluid resuscitation. However, on the battlefield, two factors have prevented prompt and aggressive treatment. First, the amount of resuscitative fluid that is available is limited by the weight a soldier can carry. Also, it is often difficult to recognize the adequacy of organ perfusion in a battlefield environment. Thus, the inability for personnel at a trauma site to obtain feedback on the effectiveness of fluid resuscitation in a timely manner can materially affect eventual outcome.

SUMMARY

Therefore it is an object of this invention to provide a non-invasive procedure and process for evaluating the efficacy of fluid resuscitation therapy for hemorrhagic shock.

Another object of this invention is to provide a non-invasive procedure and process for use by paramedics in evaluating the efficacy of fluid resuscitation therapy for hemorrhagic shock.

Yet another object of this invention is to provide a non-invasive procedure and process for evaluating the efficacy of fluid resuscitation for hemorrhagic shock that is easy to use by personnel at a trauma site.

Still another object of this invention is to provide apparatus for performing a non-invasive procedure and process for evaluating the efficacy of fluid resuscitation therapy for hemorrhagic shock.

Yet still another object of this invention is to provide apparatus for performing a non-invasive procedure and process for use by paramedics in evaluating the efficacy of fluid resuscitation therapy for hemorrhagic shock.

Still yet another object of this invention is to provide apparatus for performing a non-invasive procedure and process for evaluating the efficacy of fluid resuscitation for hemorrhagic shock that is easy to use by personnel at a trauma site.

In accordance with this invention an indication of mean arterial pressure is obtained by acquiring data samples that represent the moisture content at a selected area of a patient's perfused tissue. The acquired data samples are then converted to a reading for display that correlates with mean arterial pressure.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
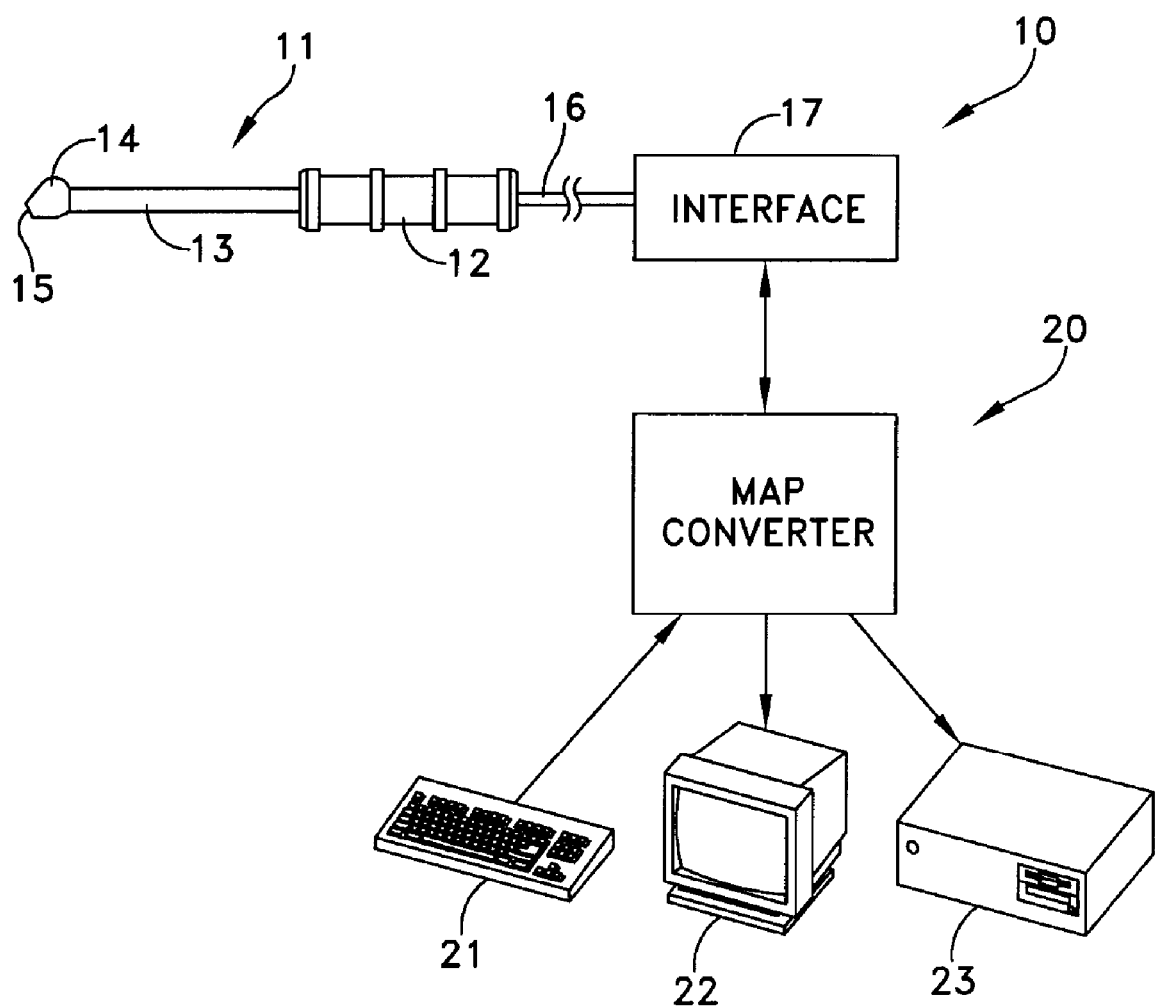
FIG. 1 depicts the apparatus embodying this invention for obtaining measurements of mean arterial pressure as an indication of the effectiveness of fluid resuscitation therapy.

FIG. 1 depicts apparatus for obtaining readings correlated to Mean Arterial Pressure, which apparatus includes a dermal phase meter 10 with a probe 11. The probe 11 includes a handle 12 at a proximal end with an extension 13 intermediate the handle 12 and a distal tip 14. The distal tip has a measuring surface 15 that can have a variety of forms.

Essentially the surface 15 is defined by two electrodes spaced by an insulating material. In this embodiment the outer portion of the tip forms an outer cylindrical or annular electrode. A rod forms an inner electrode. The insulating material has an annular form and is disposed between the outer and inner electrodes.

Conductors 16 couple the electrodes in the distal tip 14 to an interface 17 that includes various electronics for sampling data to read the signal developed across the electrodes at some sampling frequency.

U.S. Pat. No. 6,370,426 (2002) discloses a method and apparatus for measuring relative hydration of a substrate is an example of a dermal phase meter 10 that can be used to implement this invention.

A MAP converter 20 controls the operation of the probe 11 through the interface 17. The MAP converter 20 connects to an input device shown in the form of a keyboard 21, and one or more output devices, shown as a video display 22 and a hard copy printing device 23. As will be apparent the specific implementation of the MAP converter 20 can take many forms that are well within the purview of persons of ordinary skill in the art.

Figure 2:
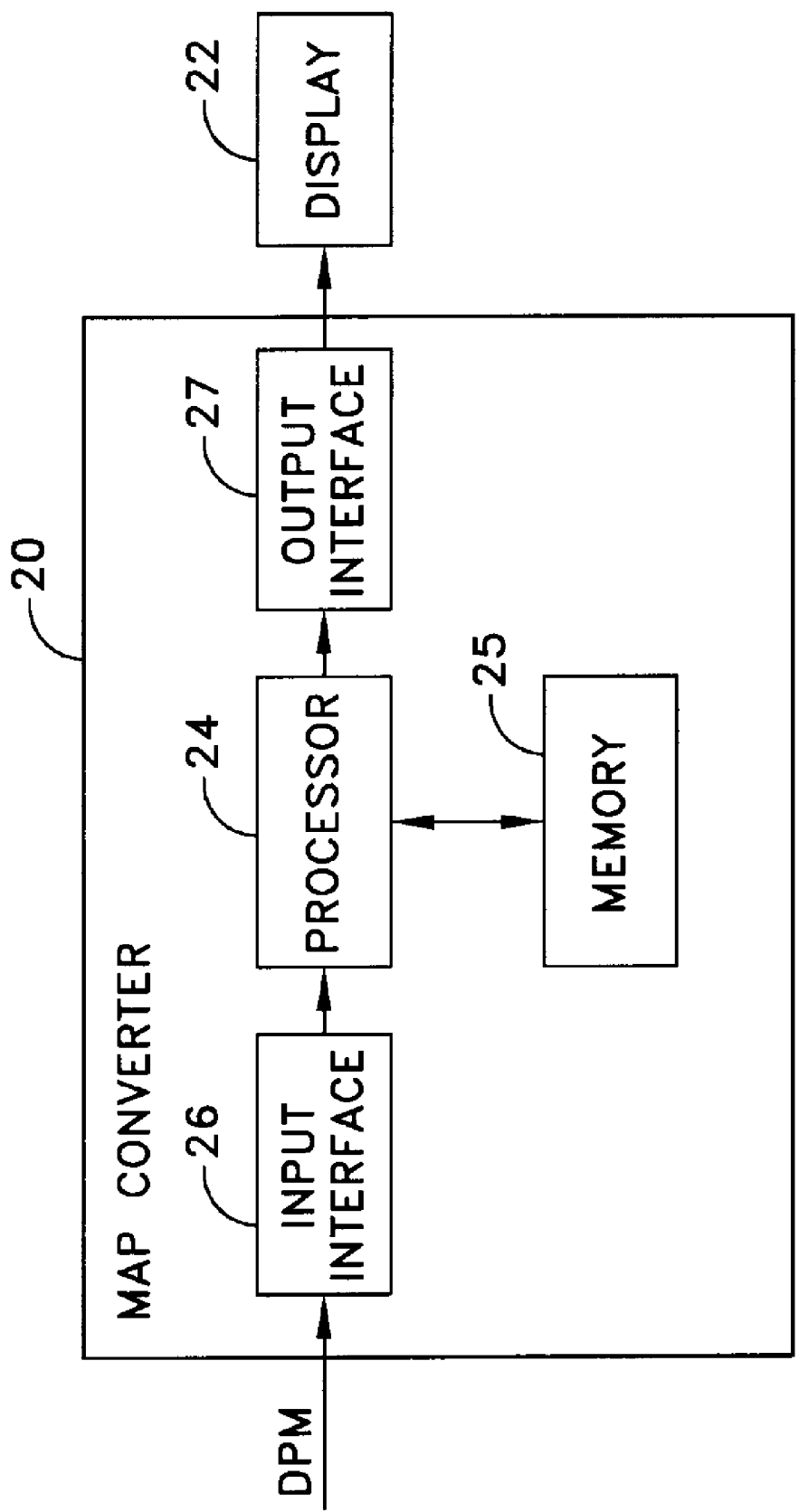
FIG. 2 is a block diagram of one embodiment of a control as shown in FIG. 1.

An example of a MAP converter 20 is shown in FIG. 2 as including a processor 24 with a memory 25. The processor 24 and memory 25 interact to receive DPM signals from the interface 17 through an input interface 26. An output interface 27 transfers signals to one or more output devices. As will be apparent, the MAP converter 20 and display 22 could be implemented in a personal computer or other similar device that has the capacity for receiving the DPM signal, for performing the necessary data storage and analysis as will be described, and for providing an MAP reading.

Figure 3:
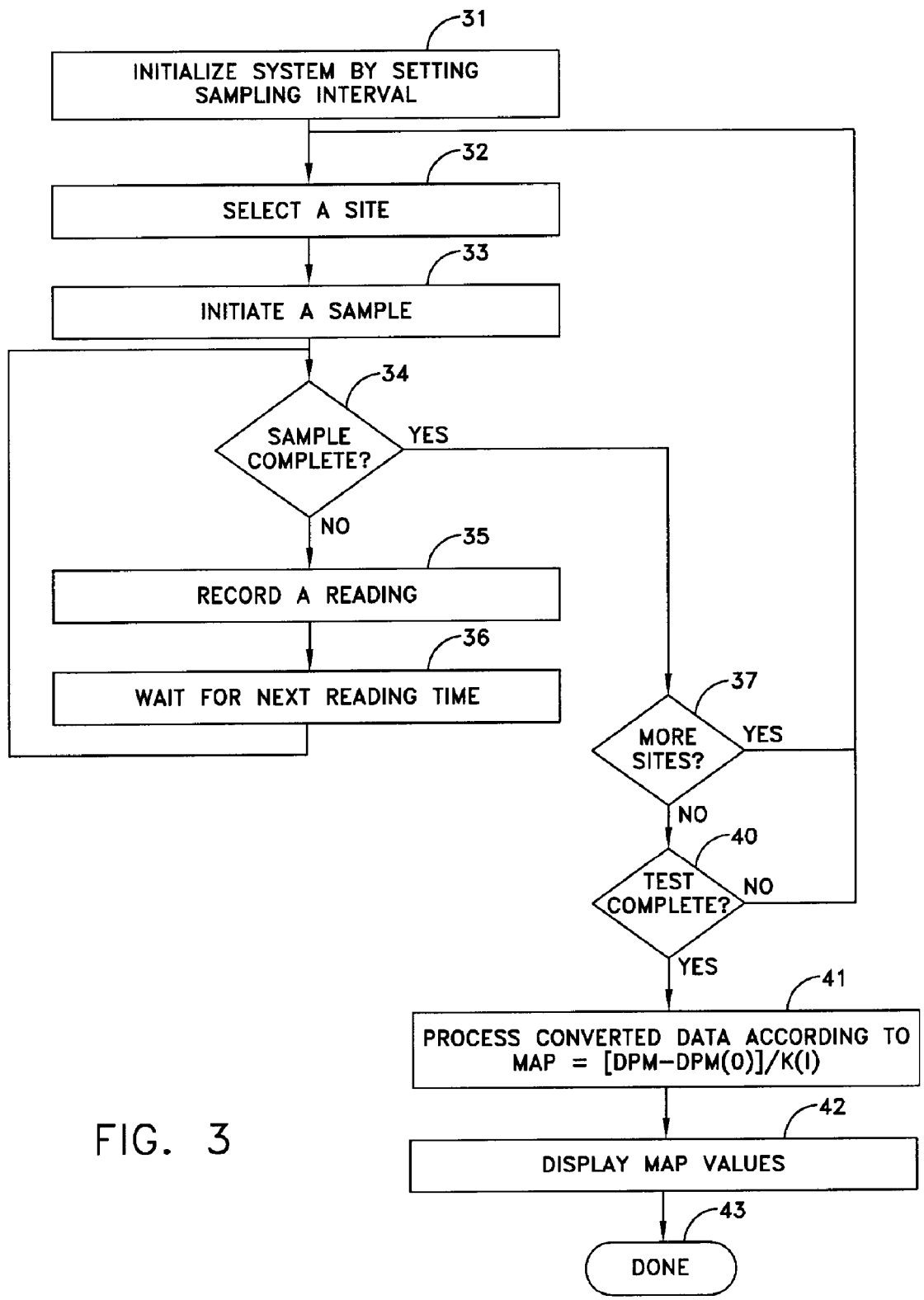
FIG. 3 is a flow diagram of the procedures used to process data obtained during a measurement in accordance with this invention.

FIG. 3 depicts one procedure for implementing this invention as can be performed in a computer-based MAP converter 20. Before discussing this procedure, it will be helpful to understand variations in the protocol for making these measurements and some basic operational characteristics of a dermal phase meter. A dermal phase meter, such as the DPM-9003 dermal phase meter, generates a series of discrete readings at a frequency generally set by the manufacturer, but, in some embodiments, by the user. The rate at which such readings are taken is a reading rate and a reading time represents the time between successive readings. A sample comprises a set of readings. The set can be delimited by time or reading values. For the assessment of this invention, it is assumed that time will delimit the sample. In one assessment protocol the sample time begins shortly after the probe contacts the tissue at a site and terminates about ten seconds later.

As an assessment may involve taking samples from one or more perfused tissue areas, such as in the inner ear canal, mucous membrane of the tongue or nasal passage, the anus, the sub-lingual or any other area of perfused tissue. An assessment may also involve taking successive sets of multiple samples from different perfused tissue areas with readings for a first area in a set starting some time interval after the readings for a prior set at another area have been completed.

The process shown in FIG. 3 for obtaining MAP readings begins by initializing the system in step 31. In the particularly disclosed implementation of FIG. 3, the person running the system 10 sets sample time. That is, the person will identify the time during which readings are taken. Step 31 would also include setting other variables, such as the reading time, if such initialization was necessary.

Step 32 selects a site for testing. This provides the operator with the possibility of taking readings from a single or multiple sites. Step 33 initiates the readings for the sample once the probe 11 is properly located at a site within a patient's mouth.

Step 34 is a loop control for receiving and recording data readings from the DPM interface 17 in FIG. 1. Initially step 34 transfers control to step 35 that records a data reading usually in a time-stamped format. Step 36 then establishes a wait interval corresponding to the reading time. This loop continues until the test sample has been completed as defined in step 31 whereupon control transfers to step 37.

Step 37 represents a step whereby the person conducting the assessment determines whether additional sites are to be sampled. If more sites are to be sampled, control transfers back to step 32 to perform the selection by moving the probe 11 to another site. Thus, the loop comprising steps 32 through 37 could be used to take a single sample from multiple sites, for example.

When all the sites have been sampled, step 37 transfers control to step 40 that represents another control point for the person administering the diagnoses. A test could be considered complete if all the sites have been measured one time. If the test is to involve multiple samples from multiple sites, step 40 transfers control back to step 32 to produce another set of samples. Although not shown, it will be apparent that step 40 could include some time interval or delay or other parameter to control the circumstances under which control would transfer.

When the test is complete, step 40 transfers control to step 41 that converts this sampling to the MAP values and displays the MAP values at step 42, for example at the display 22 in FIGS. 1 and 2. Then step 43 terminates the process of FIG. 3.

Figure 4:
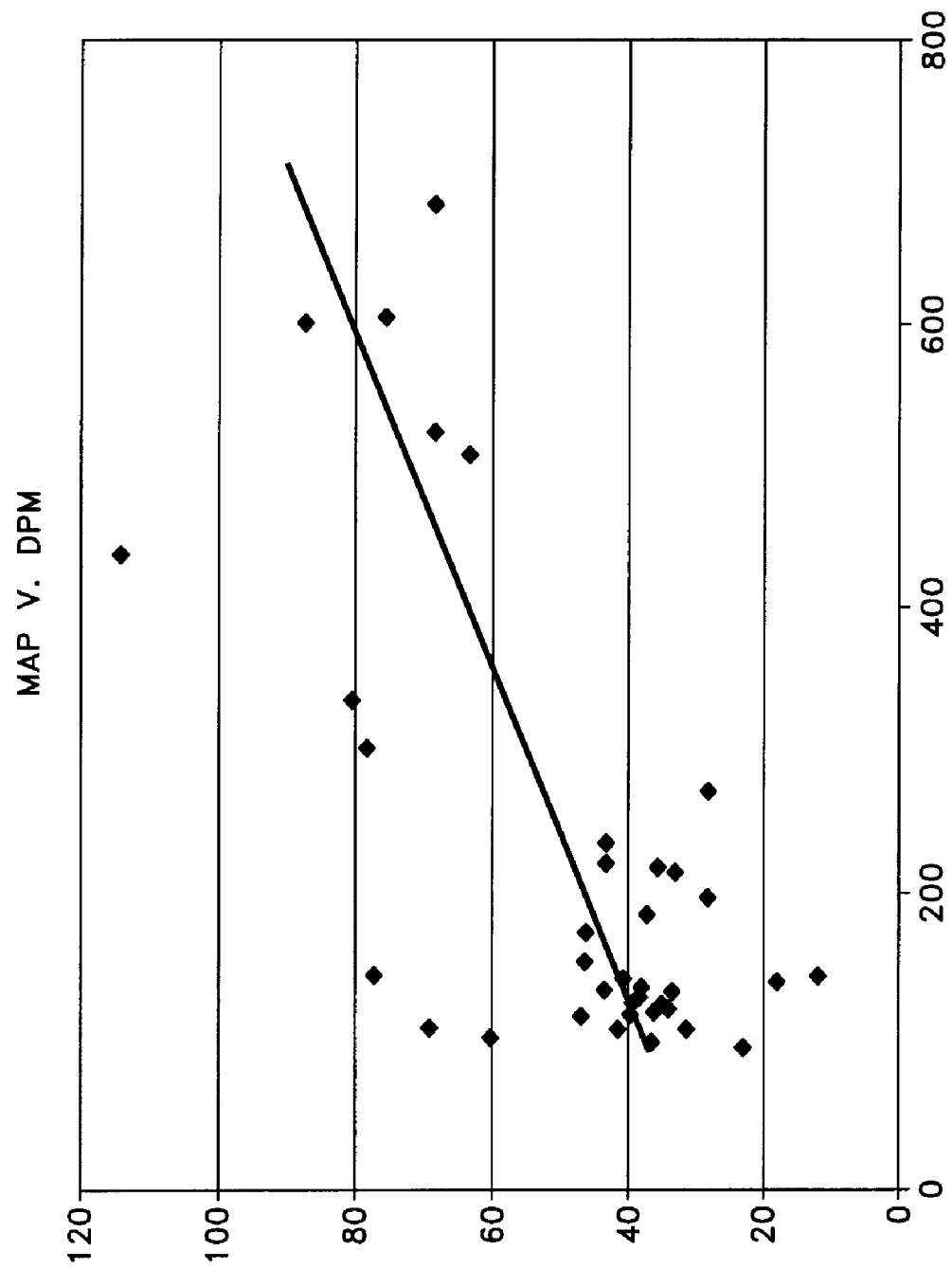
FIG. 4 depicts one relationship between measurements taken by the apparatus in FIG. 1 and mean arterial pressure.

FIG. 4 depicts a relationship between the average DPM readings with respect to Mean Arterial Pressure. The DPM readings were taken at the nasal septum and auditory canal of a pig. In FIG. 4 this relationship is linear. The slope of this graph then represents the corresponding K(I) constant.

The graph in FIG. 4 exhibits a strong correlation between average DPM readings and measured Mean Arterial Pressure values obtained by invasive procedures. Letting DPM represent average DPM readings, MAP represent the corresponding relative calculated value for Mean Arterial Pressure, and $DPM_0$ represent the DPM ready for a zero MAP value. FIG. 4 defines a general correlation of:

$$DPM = K(I)MAP + DPM(0) \qquad (1)$$

Solving for MAP yields:

$$MAP = \{DPM - DPM(0)\}/K(I) \qquad (2)$$

As will be apparent K(I) will vary with each analysis. With reference to FIG. 4, K(I) is a positive number. For specifically K(I)=0.0859 and DPM(0)=28.085. Referring again to FIG. 3, step 41 selects an appropriate value of K(I) to convert the data into a MAP reading if such a selection is available.

It will now be apparent that the apparatus in FIGS. 1 and 2 combined with the processing according to FIG. 3, or equivalent apparatus and programming, provides readings and relative values for Mean Arterial Pressure that correlate to conventional MAP readings obtained by currently implemented highly invasive procedures. More the Mean Arterial Pressure values obtained by the use of this invention are based upon simply administered tissue measurements readily taught to nurses, paramedics and other non-physician staff. Consequently it is possible to train medical staff to perform this diagnosis at a trauma site. It will also be apparent that components of the specific structures and procedures disclosed in FIGS. 1 through 3 can be modified to facilitate use of the structure or operation of the structure. It is the intent of the appended claims to cover all such variations and modifications as come within the true spirit and scope of this invention.

This invention has been disclosed in terms of certain embodiments. It will be apparent that many modifications can be made to the disclosed apparatus without departing from the invention.

What is claimed is:

1. A method for providing a relative value of mean arterial pressure of a subject comprising the steps of:
   A. measuring tissue moisture at a selected area of perfused tissue of the subject, B. acquiring data samples of the measured moisture content at the selected area, and C. converting the collected data to a value of mean arterial pressure.

2. A method as recited in claim 1 wherein said measurement includes making successive impedance measurements at the selected area.

3. A method as recited in claim 1 wherein said measurement includes making successive impedance measurements at a plurality of areas of perfused tissue.

4. A method as recited in claim 1 wherein said converting includes generating the relative value of mean arterial pressure, MAP, according to MAP={DPM−DPM(0)}/K(I) where DPM represents the average of the impedance measurements, where DPM(0) is the value of DPM for MAP=0 and K(I) is a constant.

5. A method as recited in claim 4 wherein different values of K(I) are stored for different analyses.

6. A method as recited in claim 4 wherein said measurement includes making successive impedance measurements at the selected area.

7. A method as recited in claim 4 wherein said measurement includes making successive impedance measurements at a plurality of areas of perfused tissue.

8. A method as recited in claim 7 wherein different values of K(I) are stored for different analyses.

9. Apparatus for providing a relative value of mean arterial pressure of a subject comprising:
   A. means for measuring tissue moisture at a selected are of perfused tissue of the subject,
   B. means for acquiring data samples of the measured moisture content at the selected area, and
   C. means for converting the collected data to the relative value of mean arterial pressure.

10. Apparatus as recited in claim 9 wherein said measurement means comprises a dermal phase meter for generating successive impedance measurements at the selected area.

11. Apparatus as recited in claim 9 wherein said measurement means comprises a dermal phase meter for generating successive impedance measurements at a plurality of areas of perfused tissue.

12. Apparatus as recited in claim 9 wherein said converting means includes means for generating the relative value of mean arterial pressure, MAP, according to MAP={DPM−DPM(0)}/K(I) where DPM represents the average of the impedance measurements, where DPM(0) is the value of DPM for MAP=0 and K(I) is a constant.

13. Apparatus as recited in claim 12 including means for storing different values of K(I) for different analyses.

14. Apparatus as recited in claim 12 wherein said measurement means includes dermal phase meter means for making successive impedance measurements at the selected area.

15. Apparatus as recited in claim 12 wherein said measurement means includes dermal phase meter means for making successive impedance measurements at a plurality of areas of perfused tissue.

16. Apparatus as recited in claim 15 including means for storing different values of K(I) for different analyses.

* * * * *